US009724500B2

(12) United States Patent
Farnan et al.

(10) Patent No.: US 9,724,500 B2
(45) Date of Patent: Aug. 8, 2017

(54) BY-PASS SHUNT TO REDUCE FLOW OUTPUT OF CIRCULATORY ASSIST DEVICE

(71) Applicant: CircuLite, Inc., Saddle Brook, NJ (US)

(72) Inventors: Robert C. Farnan, Ridgewood, NJ (US); Bryan Fritz, Morristown, NJ (US); Yun Yi, Riverdale, NJ (US)

(73) Assignee: CircuLite, Inc., Teaneck, NJ (US)

( * ) Notice: Subject to any disclaimer, the term of this patent is extended or adjusted under 35 U.S.C. 154(b) by 259 days.

(21) Appl. No.: 13/692,359

(22) Filed: Dec. 3, 2012

(65) Prior Publication Data
US 2013/0150772 A1 Jun. 13, 2013

Related U.S. Application Data

(60) Provisional application No. 61/568,827, filed on Dec. 9, 2011.

(51) Int. Cl.
*A61M 27/00* (2006.01)
*A61M 1/10* (2006.01)
*A61M 1/12* (2006.01)

(52) U.S. Cl.
CPC .......... *A61M 27/002* (2013.01); *A61M 1/101* (2013.01); *A61M 1/1089* (2014.02); *A61M 1/122* (2014.02); *A61M 2205/04* (2013.01); *A61M 2205/3337* (2013.01); *A61M 2240/00* (2013.01)

(58) Field of Classification Search
CPC ............................ A61M 1/1089; A61M 1/122
USPC .......................................................... 604/9
See application file for complete search history.

(56) References Cited

U.S. PATENT DOCUMENTS

| 5,267,940 A * | 12/1993 | Moulder ................... A61F 2/06 600/16 |
| 5,814,004 A | 9/1998 | Tamari |
| 2005/0234287 A1 | 10/2005 | Weatherbee |
| 2006/0052737 A1* | 3/2006 | Bertrand ............. A61M 1/0031 604/9 |
| 2006/0264800 A1* | 11/2006 | Bolling et al. ..................... 604/9 |
| 2008/0199357 A1 | 8/2008 | Gellman et al. |

FOREIGN PATENT DOCUMENTS

| WO | 2004054641 A1 | 7/2004 |
| WO | 2009127704 A1 | 10/2009 |
| WO | 2010048644 A1 | 4/2010 |

OTHER PUBLICATIONS

European Patent Office, International Search Report and Written Opinion in PCT Application No. PCT/US2012/068184, Oct. 15, 2013.
European Patent Office, Invitation to Pay Additional Fees in PCT Application Serial No. PCT/US2012/068184, Mar. 27, 2013.

* cited by examiner

*Primary Examiner* — Leslie Deak
*Assistant Examiner* — Kai Weng
(74) *Attorney, Agent, or Firm* — Wood Herron & Evans LLP

(57) ABSTRACT

A by-pass shunt for use with a bodily fluid pump. The by-pass shunt includes an inflow conduit, an outflow conduit, and an intermediate conduit fluidically coupling the inflow and outflow conduits. A flow restrictor is operably coupled to a portion of the intermediate conduit and is configured to reduce a fluid flow from the outflow conduit, through the intermediate conduit, and into the inflow conduit.

4 Claims, 10 Drawing Sheets

BY-PASS SHUNT TO REDUCE FLOW OUTPUT OF CIRCULATORY ASSIST DEVICE

CROSS-REFERENCE TO RELATED APPLICATION

This application claims the benefit of U.S. Provisional Patent Application Ser. No. 61/568,827, filed on Dec. 9, 2011, the disclosure of which is incorporated by reference herein, in its entirety.

FIELD OF THE INVENTION

The present invention relates generally to cardiac assist devices and, more particularly, to adjustable cardiac assist devices.

BACKGROUND

The human heart is the muscle that is responsible for pumping blood throughout the vascular network. Veins are vessels that carry blood toward the heart while arteries carry blood away from the heart. The human heart consists of two atrial chambers and two ventricular chambers. Atrial chambers receive blood from the body and the ventricular chambers, which include larger muscular walls, pump blood from the heart.

For the vast majority of the population, the events associated with the movement of blood happen without circumstance. However, for others the heart fails to provide adequate pumping capabilities. These heart failures may include congestive heart failure (commonly referred to as heart disease), which is a condition that results in any structural or functional cardiac disorder that impairs the ability of the heart to fill with or pump blood throughout the body. Presently, there is no known cure for heart disease and long-term treatment is limited to a heart transplant.

While the wait-list for receiving a heart continues to grow, alternative measures, such as circulatory assist devices, can at least temporary improve the quality of life of those patients on the wait-list. These systems were developed to provide assistance to the heart by way of a mechanical pump. Blood may then be circulated throughout the vascular network despite the diseased heart tissue. Traditionally, these circulatory assist devices include an implantable or extracorporeal pump, a controller (internal or external), and inflow and outflow cannulae connecting the pump to structures within the vascular system.

Circulatory assist devices offer great symptom relief to adult patients. However, pediatric patients, whose cardiac output demand changes over time, may require several follow-up surgeries to replace their existing mechanical pump with another pump capable of greater fluid output. Not only does this create a surgical risk to the pediatric patient, but the appropriate replacement mechanical pump may not be readily compatible with the previously implanted cannulae and components. Furthermore, flow adjustability mechanisms included in conventional mechanical pumps may not sufficiently reduce the blood flow for pediatric patients, and particularly, neonatal patients. Thus, there continues to be a need for circulatory assist devices that are adaptable to the ever changing cardiac demand of a growing pediatric patient.

SUMMARY OF THE INVENTION

According to one embodiment of the invention, a by-pass shunt for use with a bodily fluid pump is described. The by-pass shunt includes an inflow conduit, an outflow conduit, and an intermediate conduit fluidically coupling the inflow and outflow conduits. A flow restrictor is operably coupled to a portion of the intermediate conduit and is configured to reduce a fluid flow from the outflow conduit, through the intermediate conduit, and into the inflow conduit.

A bodily fluid pumping system is described in accordance with another embodiment of the invention. The bodily fluid pumping system includes a mechanical pump having inflow and outflow ports. An inflow cannula extends away from the inflow port and an outflow cannula extends away from the outflow port. The inflow and outflow conduits are fluidically coupled by an intermediate conduit, which further includes a flow restrictor operably coupled thereto. The flow restrictor is configured to reduce a fluid flow through the intermediate conduit.

Another illustrative embodiment of the invention is directed to a circulatory assist system. The system includes a mechanical pump having inflow and outflow ports. The inflow port is operably coupled to a first vascular structure of a patient by an inflow cannula. The outflow port is operably coupled to a second vascular structure of the patient by an outflow cannula. A by-pass shunt is configured to fluidically couple the inflow and outflow cannulae such that a first portion of the blood ejected from the pump flows through the outflow cannula to the second vascular structure while a second portion of the ejected blood flows through the by-pass shunt and reenters the pump from the inflow cannula. The by-pass shunt includes a compliant portion that is deformable between a first diameter state and a second diameter state, the former being expanded to a larger diameter than the latter. A flow restrictor is operably coupled to the compliant portion for transitioning the compliant portion between the first and second diameter states.

Yet another illustrative embodiment of the invention is directed to a method of assisting cardiac output. The method includes coupling an inflow port of a pump to a first vascular structure of a patient and the outflow port of the pump to a second vascular structure of the patient. The pump is operated such that a first portion of blood flow is directed from the outflow port to the second vascular structure and a second portion of blood flow is directed into a shunt and reenters the inflow port of the pump. The flow rate of the first portion of blood flow is adjusted by adjusting a flow rate of the second portion of blood.

Another illustrative embodiment of the invention is directed to a method of assisting cardiac output. The method includes coupling an inflow port of a pump to a first vascular structure of a patient and the outflow port of the pump to a second vascular structure of the patient. The pump is operated such that a first portion of blood flow is directed from the outflow port to the second vascular structure and a second portion of blood flow is directed into a shunt and reenters the inflow port of the pump. A portion of the shunt is deformed to either increase the first portion of blood flow by decreasing the second portion or decrease the first portion of blood flow by increasing the second portion of blood flow.

According to another embodiment of the invention, a circulatory assist system is described. The system includes a mechanical pump having inflow and outflow ports. The inflow port is operably coupled to a first vascular structure of a patient by an inflow cannula. The outflow port is operably coupled to a second vascular structure of the patient by an outflow cannula. A shunt provides fluid communication between the inflow and outflow cannulae. A mixing chamber is coupled to the outflow port and is configured to hold a volume of blood.

DETAILED DESCRIPTION

Figure 1:
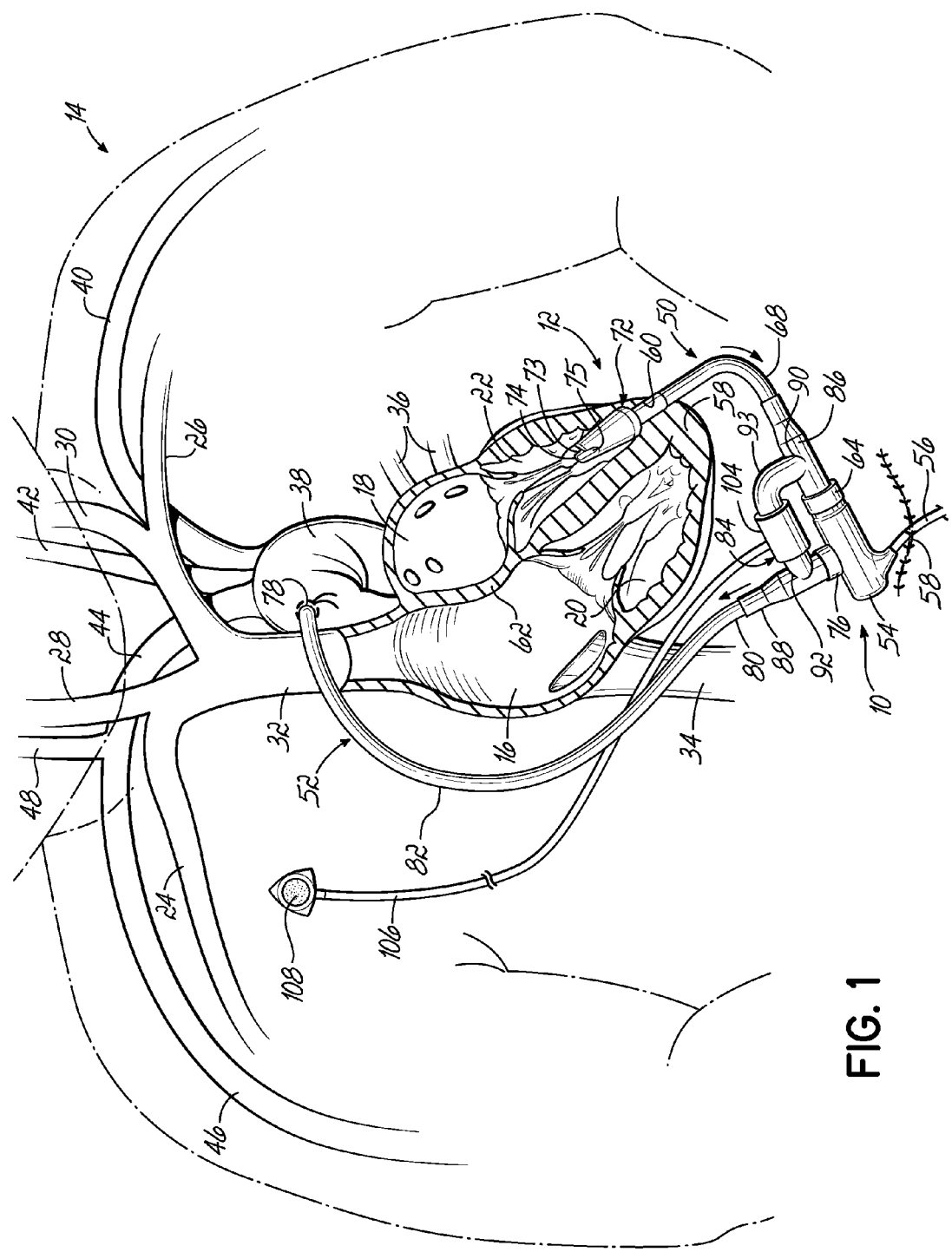
FIG. 1 is a diagrammatic view of a circulatory assist device including a by-pass shunt in accordance with one embodiment of the invention, with the heart of a pediatric patient, shown in partial cross-section.

FIG. 1 illustrates one embodiment of a circulatory assist device 10 implanted in a pediatric patient. For illustrative purposes, certain anatomy is shown including the heart 12 of the patient 14 having a right atrium 16, a left atrium 18, a right ventricle 20, and a left ventricle 22. Blood from the right and left subclavian veins 24, 26 and the right and left jugular veins 28, 30 enters the right atrium 16 through the superior vena cava 32 while blood from the lower parts of the body enters the right atrium 16 through the inferior vena cava 34. The blood is pumped from the right atrium 16, to the right ventricle 20, and to the lungs (not shown) to be oxygenated. Blood returning from the lungs enters the left atrium 18 via pulmonary veins 36 and is pumped into the left ventricle 22. Blood leaving the left ventricle 22 enters the aorta 38 and flows into the left subclavian artery 40, the left common carotid 42, and the brachiocephalic trunk 44, including the right subclavian artery 46 and the right common carotid 48.

With respect to the implanted circulatory assist device 10, two cannulae 50, 52 (inflow and outflow, respectively) extend between cardiovascular structures and a pump 54, which may be any implantable or extracorporeal pump that is radially- and/or axially-driven. Those skilled in this art, however, recognize that other types of pumps may be used in other embodiments but may include pumps such as those described in U.S. patent application Ser. No. 11/627,444, published as 2007/0197854, which is incorporated herein by reference in its entirety, or commercially-available pumps, such as the SYNERGY Pocket Micro-Pump from CircuLite, Inc. (Saddle Brook, N.J.), which is capable of delivering blood flow at rates ranging from about 3 L/min to about 4 L/min.

A cable 56 may extend transdermally from the pump 54 to a position in the abdomen where the cable 56 exits the patient 14 and connects to a power supply (not shown). Suitable power supplies may be any universal-type power supply that sends power to the pump 54 via the cable 56 and may include, but is not limited to, a rechargeable battery pack.

As illustrated, the physician may position the pump 54 within the abdomen of the patient 14. Although not shown, other locations for positioning the pump 54 are known and may also be used if desired.

Referring still to FIG. 1, the inflow cannula 50 is shown to extend from the left ventricle 22, through the apex 58, to an inflow port 64 of the pump 54. Though not shown, the inflow cannula 50 may alternatively be percutaneously delivered to intra-atrial septum 62, as was described in U.S. patent application Ser. No. 12/256,911, published as 2009/0112050, the disclosure of which is incorporated herein by reference in its entirety.

The inflow cannula 50 may be any suitable intravascular cannula device constructed from materials, such as an extruded aliphatic, polycarbonate-base polyurethane; aliphatic polyether polyurethane; aromatic polyether polyurethane; aromatic polycarbonate based polyurethane; silicone modified polyurethane; or silicone. Antimicrobial agents may be embedded within the inflow cannula material prior to the forming process to effectively reduce or eliminate the presence of a bio-film and reduce the potential for infection. Alternatively, the antimicrobial agent may be applied to the surface of the inflow cannula 50 after the molding process is complete.

A reinforcing structure may be included in the inflow cannula construction to reduce the likelihood of kink formation. The reinforcing structure may be, for example, a braided or coiled construction of a metal wire, such as stainless steel or titanium wire, or a polymeric material, such as KEVLAR (E.I. du Pont de Nemours and Co., Wilmington, Del.). The construction material may have various cross-sectional shapes, including, but not limited to, round and rectangular. If a round wire is used, the wire diameter may typically vary from about 0.001 inch (0.0254 mm) to about 0.005 inch (0.127 mm). If the material has a rectangular cross-section, the rectangle may typically have a height ranging from about 0.001 inch (0.0254 mm) to about 0.005 inch (0.127 mm) and a width ranging from about 0.003 inch (0.0762 mm) to about 0.010 inch (0.254 mm).

While not necessary, the illustrative inflow cannula 50 may be tapered distally from the proximal end 68, which accommodates the larger diameter inflow port 64 of the pump 54 proximally, and the smaller diameter body of the cannula 50 accommodates the smaller anatomical structures of the pediatric patient 14. For example, the smaller diameter body of the inflow cannula 50 may range from about 3 mm to about 7 mm while the larger diameter proximal end 68 may range from about 8 mm to about 11 mm.

A distal end of the inflow cannula 50 may include a tip 73, which is described in greater detail in U.S. patent application Ser. No. 13/025,757, incorporated herein by reference in its entirety. The illustrative tip 73 includes one or more openings 73 that extend proximally from a distal tip end 74. The openings 73 permit the flow of blood from the left ventricle 22 into a lumen 75 of the inflow cannula 50 even in the event that the distal tip end 74 becomes obstructed with tissue from within the left ventricle 22. The tip 73 may be constructed from a polished titanium or other suitable material and have a design that reduces fluidic turbulence and the risk of thrombosis formation. The tip design may also facilitate the coupling of the tip 73 to the distal end of the inflow cannula 50. For example, in some embodiments, a proximal end of the tip 73 may include one or more barbs (not shown) to provide resistance against undesired removal of the tip 73 from the inflow cannula 50.

The outflow cannula 52 extends from an outflow port 76 of the pump 54 to an arterial access site 78, which is illustrated herein as within the right subclavian artery 46. The outflow cannula 52 may include a construction that is generally similar to the inflow cannula 50; however, a distal end of the outflow cannula 52 is configured to be secured to the arterial access site 78. Accordingly, the distal end may be secured by one or more sutures and/or include one or more anastomotic connectors (not shown), such as those taught in U.S. patent application Ser. No. 12/829,425, the disclosure of which is incorporated herein by reference, in its entirety. The outflow cannula 52 may be tapered distally, similar to the inflow cannula 50, so that a proximal end 80 has a larger diameter that accommodates the outflow port 76 of the pump 54 and a smaller diameter cannula body 82 accommodates the anatomy of the pediatric patient 14. Again, for exemplary purposes only, the proximal end 80 may have a diameter that ranges from about 8 mm to about 11 mm while the diameter of the cannula body 82 may range from about 3 mm to about 7 mm.

Turning now to the details of the pump 54, the inflow port 64 and the outflow port 76 are coupled by a by-pass shunt 84 according to one embodiment of the present invention. The details of the by-pass shunt 84 are provided in greater detail with reference to FIGS. 2-3B.

Figure 2:
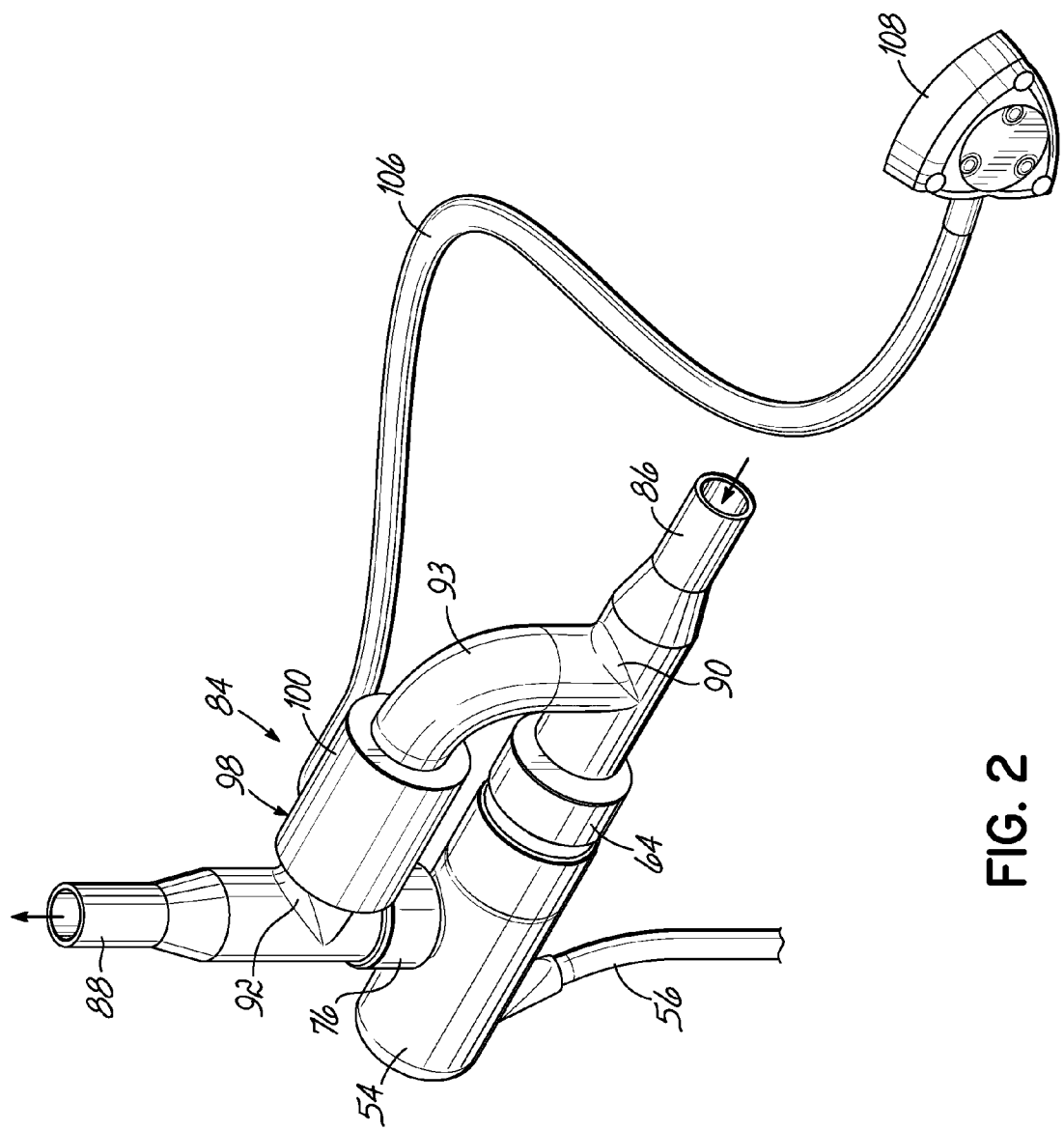
FIG. 2 is a perspective view of the circulatory assist device of FIG. 1.
Figure 3A:
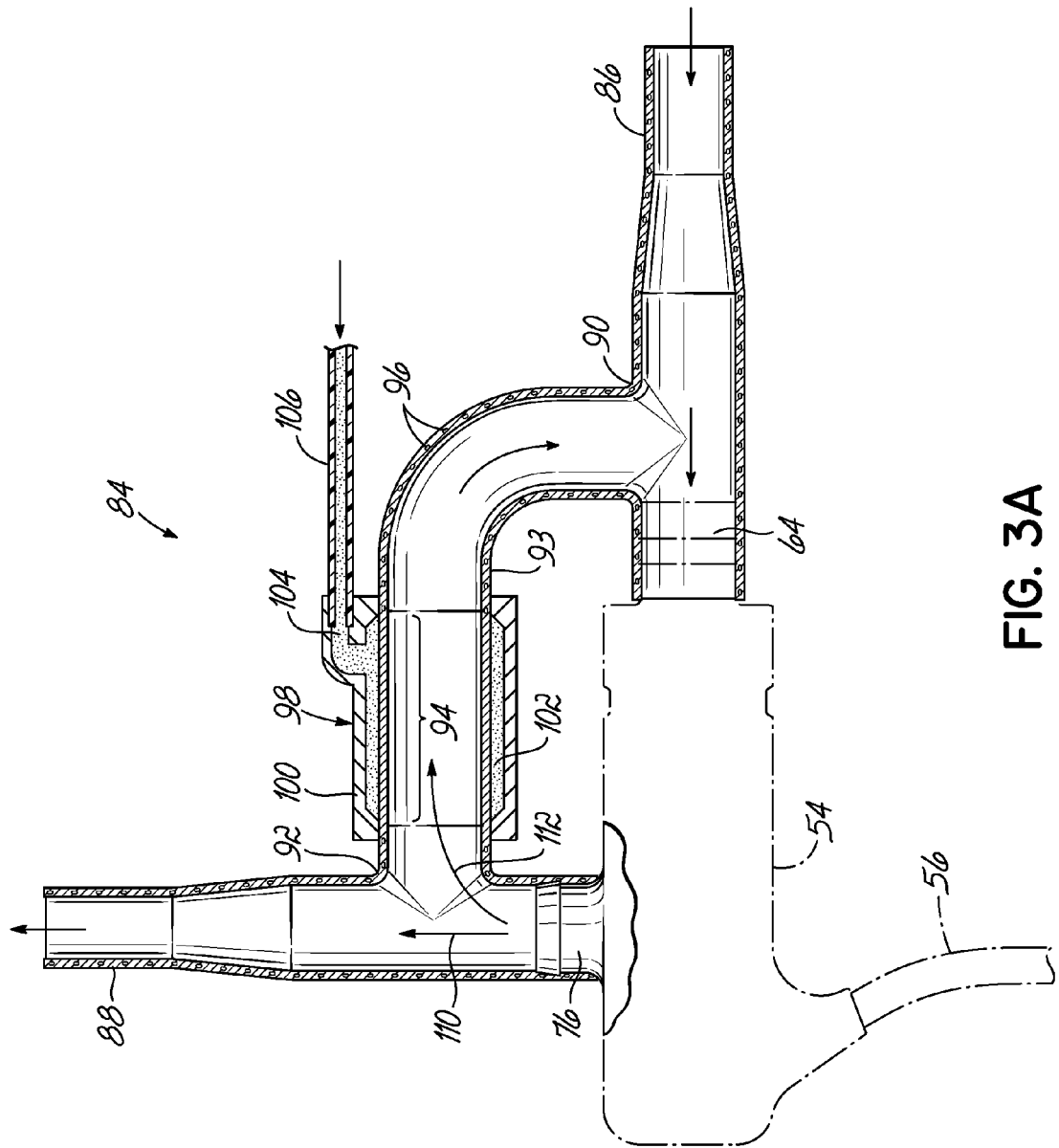
FIG. 3A is a cross-sectional view of the circulatory assist device of FIG. 2, showing the by-pass shunt configured to reduce circulatory support.
Figure 3B:
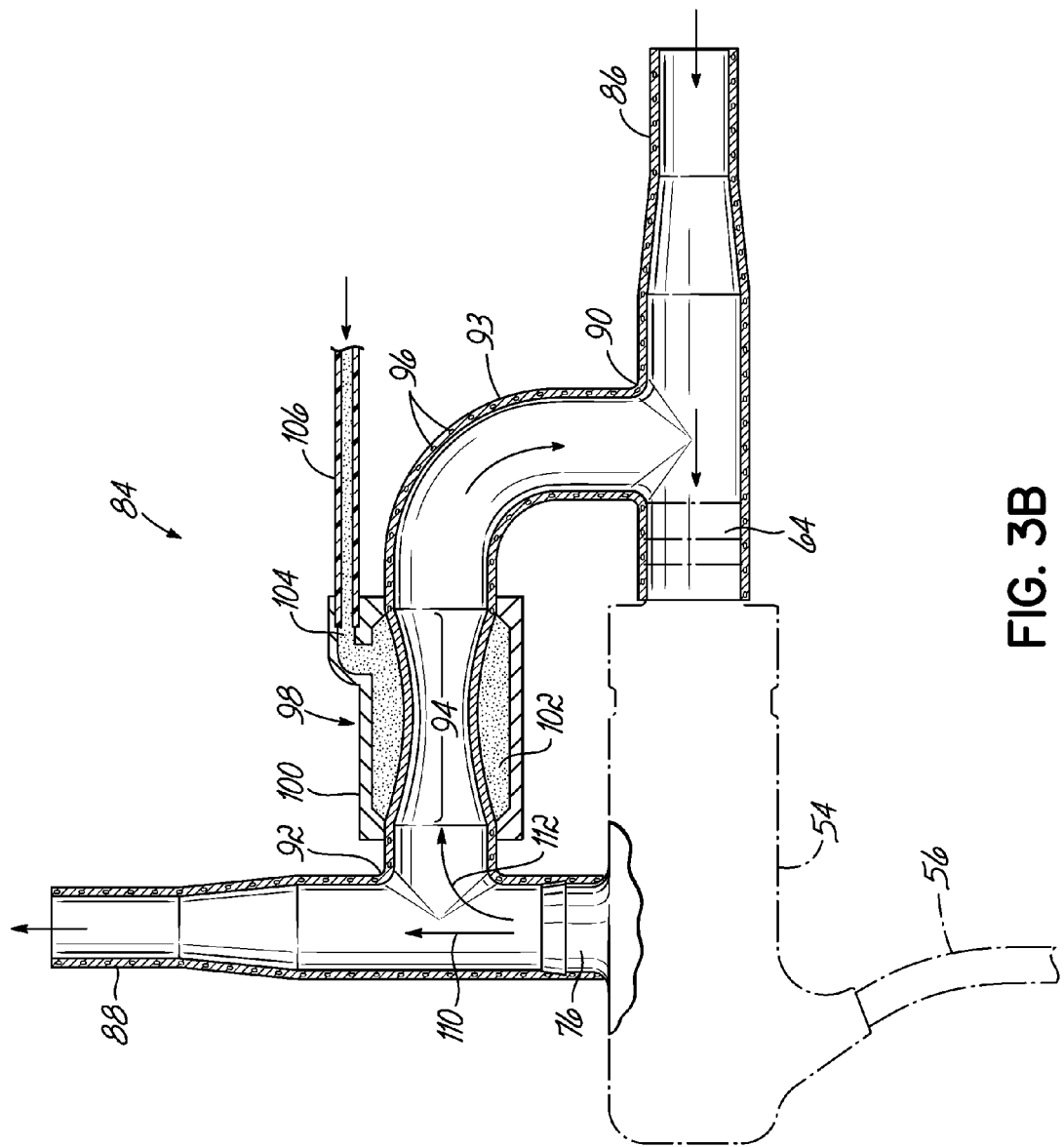
FIG. 3B is a cross-sectional view of the circulatory assist device of FIG. 2, showing the by-pass shunt configured to increase circulatory support.

In FIGS. 2-3B, the by-pass shunt 84 is shown to include an inflow conduit 86 that connects the inflow port 64 of the pump 54 to the inflow cannula 50 (FIG. 1) and an outflow conduit 88 that connects the outflow port 76 of the pump 54 to the outflow cannula 52 (FIG. 1). A first bifurcation 90 extends from the inflow conduit 86 and is positioned distal to the inflow port 64. The angle formed between the first bifurcation 90 and the inflow port 64 may vary greatly, though angles that are less than about 90° may be preferred. A second bifurcation 92 extends from the outflow conduit 88 and is positioned distal to the outflow port 76. The second bifurcation 92 may be positioned from about 4 mm to about 40 mm downstream of the outflow port 76. Again, the angle formed between the second bifurcation 92 and the outflow port 76 may vary, though angles that are less than about 90° may be preferred. The bifurcations 90, 92 are joined by an intermediate conduit 93.

While the intermediate conduit 93 is specifically shown as extending between the inflow conduit 86 and the outflow conduit 88, it would be readily appreciate that in alternate embodiments, the intermediate conduit 93 may extend between the inflow and outflow cannula 50, 52 (FIG. 1) or between one of the inflow and outflow conduits 86, 88 and one of the inflow and outflow cannula 50, 52 (FIG. 1).

The by-pass shunt 84 may be constructed in a manner that is generally similar to the inflow and outflow cannulae 50, 52. That is, the walls comprising the by-pass shunt 84 may include an extruded aliphatic, polycarbonate-base polyurethane; aliphatic polyether polyurethane; aromatic polyether polyurethane; aromatic polycarbonate based polyurethane; silicone modified polyurethane; or silicone. Antimicrobial agents may be embedded within the by-pass shunt 84 prior to the forming process to effectively reduce or eliminate the presence of a bio-film and reduce the potential for infection. Alternatively, the anti-microbial agent may be applied to the surfaces of the by-pass shunt 84 after the molding process. The walls of the by-pass shunt 84 generally include a reinforcing structure 96, which is similar to the reinforcing structure construction of the inflow and outflow cannulae 50, 52. However, a portion of the by-pass shunt 84 between the first and second bifurcations 90, 92 is constructed to be at least partially deformable (or more compliant than surrounding portions, i.e., a compliant portion 94). One manner of increasing the compliancy of the compliant portion 94 could include forming the portion without the reinforcing structure 96; however, other methods of construction would be known.

As shown in FIG. 2, and perhaps more clearly shown in FIGS. 3A and 3B, a by-pass flow restrictor 98 surrounds the compliant portion 94. In this particular embodiment, the by-pass flow restrictor 98 includes a housing 100 that surrounds an outer surface of the compliant portion 94 and forms a fluid-tight cavity 102 that is adjacent to and surrounding the compliant portion 94. A fluid port 104 and a refill line 106 fluidically couple the fluid-tight cavity 102 to a refill port 108, which may be constructed, for example, in a manner similar to a vascular access port. The refill line 106 may extend from the fluid port 104 to a position within the chest cavity where the refill line 106 and refill port 108 reside external to the patient 14 (FIG. 1). Alternatively, the refill line 106 and the refill port 108 may be positioned subcutaneously and, optionally, submuscularly. The refill port 108 is configured to receive an inflation fluid, such as saline, that may be injected via a syringe (not shown).

Use of the by-pass shunt 84 is described with reference to FIGS. 3A and 3B. FIG. 3A illustrates the by-pass shunt 84 as it would be implanted and used in a pediatric patient 14 (FIG. 1) having a lower cardiac output demand. Specifically, the by-pass flow restrictor 98 is illustrated in a first state where little-to-no fluid is injected into the fluid-tight cavity 102 and substantially no fluidic pressure is applied to the compliant portion 94. Therefore, the diameter of the lumen within the compliant portion 94 is unrestricted, or in a first, expanded state (e.g., a larger diameter). As a result, blood flowing into the pump 54 from the inflow conduit 86 is directed out of the pump 54 through the outflow port 76 and into the outflow conduit 88. A first portion of the blood (represented by arrow 110) exiting the pump 54 (i.e., the outflowing blood) continues into the lumen of the outflow cannula 52 (FIG. 1) to the arterial access site 78 (FIG. 1); and a second portion of the outflowing blood (represented by arrow 112) is diverted at the second bifurcation 92, traverses the compliant portion 94, and reenters the inflow conduit 86 at the first bifurcation 90. Thus, the total flow of blood into the arterial access site 78 (FIG. 1) is reduced by at least the second portion (arrow 112) as compared to a circulatory assist device operating without the illustrated by-pass shunt 84. In some embodiments, the flow of blood into the arterial access site 78 (FIG. 1) may be as low as about 0.1 L/min or about 0.3 L/min (second flow may range from about 2.7 L/min to about 3.9 L/min.), which is at least partially dependent on the fluid output of the particular implantable pump and the diameter of the first expanded state of the compliant portion 94.

As the pediatric patient 14 (FIG. 1) grows and cardiac output demand increases, the physician may configure the by-pass shut 84 to redistribute the first and second portions of blood (arrows 110, 112). According to one embodiment of the invention, the physician reconfigures the by-pass shunt 84 by constricting the diameter of the compliant portion 94.

One manner of constricting the diameter of the compliant portion 94 is shown in FIG. 3B. Accordingly, the physician injects additional inflation fluid into the refill port 108 (FIG. 2), which flows through the refill line 106 and into the fluid-tight cavity 102. Increasing the volume of inflation fluid within the fluid-tight cavity 102 increases the fluidic-pressure within the fluid-tight cavity 102 and applies a radially, inwardly-directed force onto the compliant portion 94 such that the compliant portion 94 deforms and the lumen diameter is reduced to a second condensed state (e.g., a smaller diameter). As a result of the second condensed state, the volume of the second portion of blood (arrow 112) is decreased as compared to the configuration in FIG. 3A, thereby increasing the first portion of blood (arrow 110) flowing into the arterial access site 78 (FIG. 1). In some embodiments, the first portion of blood (arrow 110) flowing into the arterial access site 78 (FIG. 1) may be increased from the lower flow rates (i.e., about 0.1 L/min to about 0.3 L/min) to approximately the fluid output of the particular implantable pump, which may range as high as about 3.0 L/min to about 4.0 L/min, depending on the particular mechanical pump in use.

It will be readily appreciated by one of ordinary skill in the art that the fluid pressure within the fluid-tight cavity 102 of the by-pass flow restrictor 98 may be intermittently adjusted from time-to-time. That is, the walls of the compliant portion 94 may be deformed, in either direction and by varying degrees, over time, to continuously adjust for the changing cardiac output demands of the growing pediatric patient 14 (FIG. 1).

It will be further appreciated that in alternative, or in addition, to the restriction of the second portion of blood flow, the physician may also alter the operating speed of the mechanical pump 54. The combination of the deformed compliant portion 94 and the operating speed of the pump 54 may allow the physician to repeatedly adjust the functionality of the circulatory assist system 10 (FIG. 1), without surgery, for the individualistic and varying needs of the pediatric patient 14 (FIG. 1).

Figure 4A:
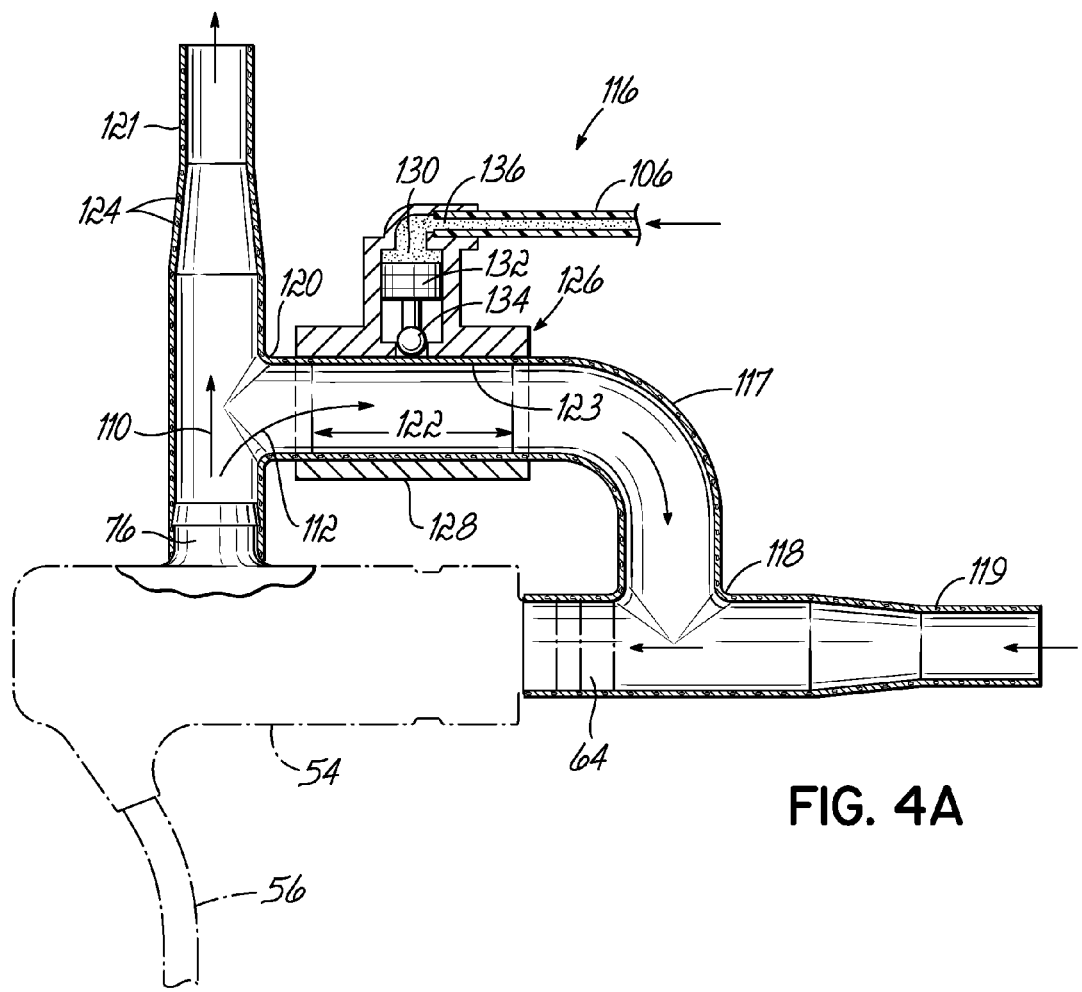
FIG. 4A is a cross-sectional view of a circulatory assist system, including a by-pass shunt in accordance with another embodiment of the invention, showing the by-pass shunt configured to reduce circulatory support.
Figure 4B:
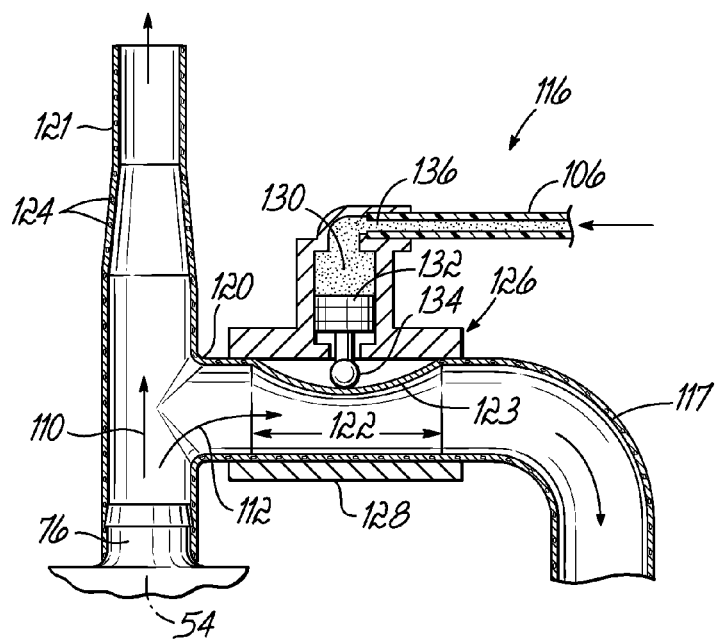
FIG. 4B is a cross-sectional view of the circulatory assist device of FIG. 4A with the by-pass shunt configured to increase circulatory support.

FIGS. 4A and 4B illustrate a by-pass shunt 116 in accordance with another embodiment of the invention. In particular, the by-pass shunt 116 includes a conduit 117 extending between first and second bifurcations 118, 120 associated with the inflow and outflow conduits 119, 121, respectively, and further includes a compliant portion 122 having at least one wall 123 that is deformable. For example, the wall 123 may be molded in a manner that is similar to the other walls comprising the by-pass shunt 116 but without including the reinforcing structuring 124.

A by-pass flow restrictor 126 surrounds the compliant portion 122 and includes a housing 128 having a piston chamber 130. A piston 132 residing within the piston chamber 130 is positioned orthogonal to the wall 123 and includes an engagement member 134 that is configured to be actuated toward and contact the wall 123. The piston chamber 130 includes a fluid-tight construction and is fluidically coupled to the refill line 106 and refill port 108 via an inflow port 136.

As shown in FIG. 4A, the by-pass shunt 116 may be configured for use in a pediatric patient 114 (FIG. 1) having a lower cardiac output demand. Accordingly, little-to-no fluidic pressure is applied to the piston chamber 130 such that the wall 123 is in a first, expanded state and the lumen of the compliant portion 122 is near a maximum. As the cardiac output demand of the patient 14 (FIG. 1) increases, the physician may inject additional inflation fluid into the refill port 108 (FIG. 1), which pressurizes the refill line 106 and piston chamber 130. The increase in fluidic pressure within the piston chamber 130 creates a force onto the piston 132 in a direction toward the wall 123. With sufficient increase in the fluidic pressure, and as shown in FIG. 4B, the piston 132 moves toward the wall 123 such that the engaging member 134 contacts and deflects the wall 123 and decreases the diameter of the lumen of the compliant portion 122. As a result, the second portion of the outflowing blood (arrow 112) that is diverted at the bifurcation 120 is reduced as compared to the second portion (arrow 112) illustrated in FIG. 4A, and the volume of the first portion of blood (arrow 110) to the arterial access site 78 (FIG. 1) is increased.

Figure 4C:
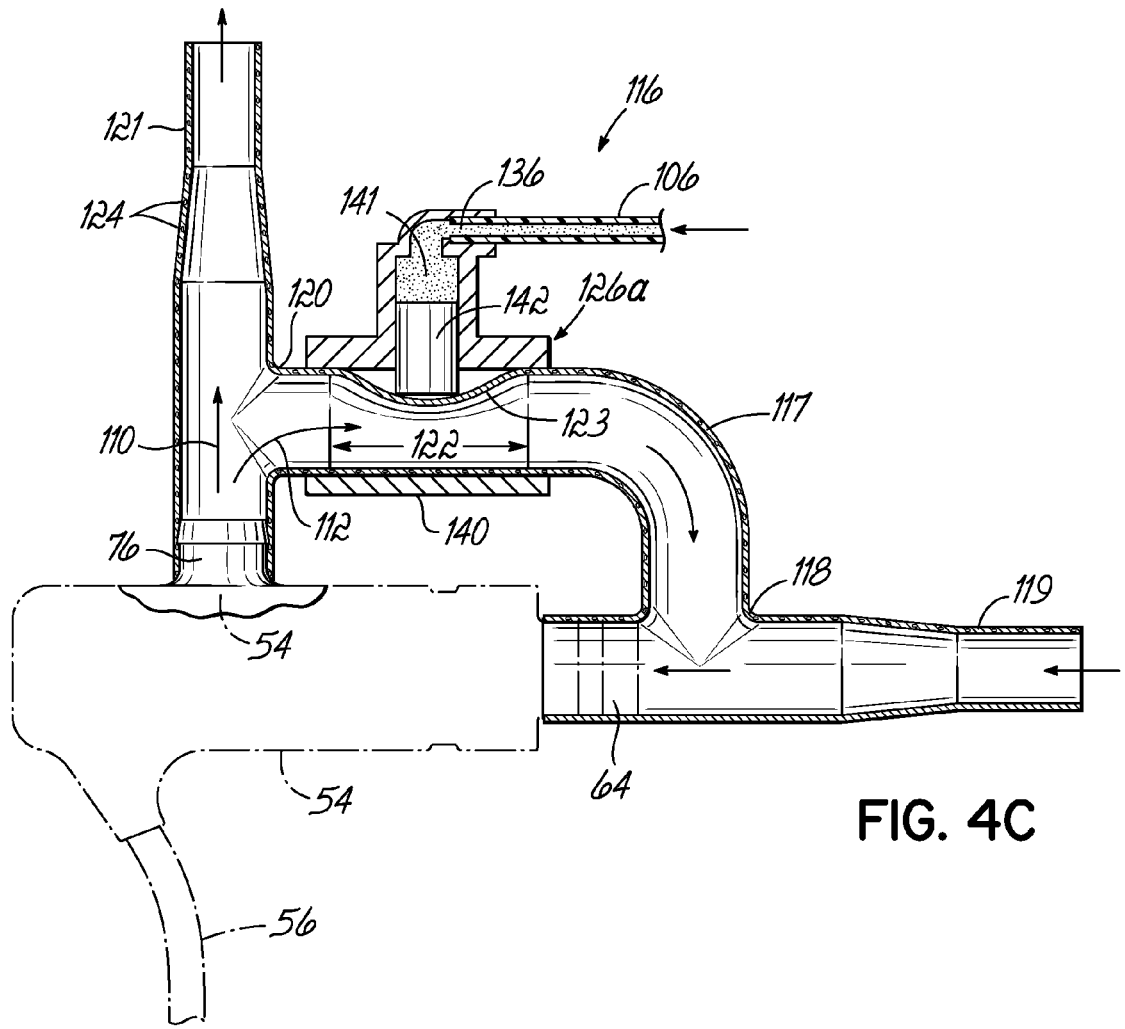
FIG. 4C is a cross-sectional view of the circulatory assist device of FIG. 4A with another embodiment of a by-pass shunt.

FIG. 4C illustrates a similar embodiment of the by-pass shunt 116 of FIG. 4A having a by-pass flow restrictor 126a that is similar to the by-pass flow restrictor 126 (FIG. 4A) but having a housing 140 that surrounds a piston chamber 141 with a piston pusher 142 positioned therein. The piston pusher 142 operates in a manner that is similar to the piston 132 (FIG. 4A) and engagement member 134 (FIG. 4A) but contacts a larger surface area of the compliant wall 123 than the engagement member 134 (FIG. 4A).

Figure 5:
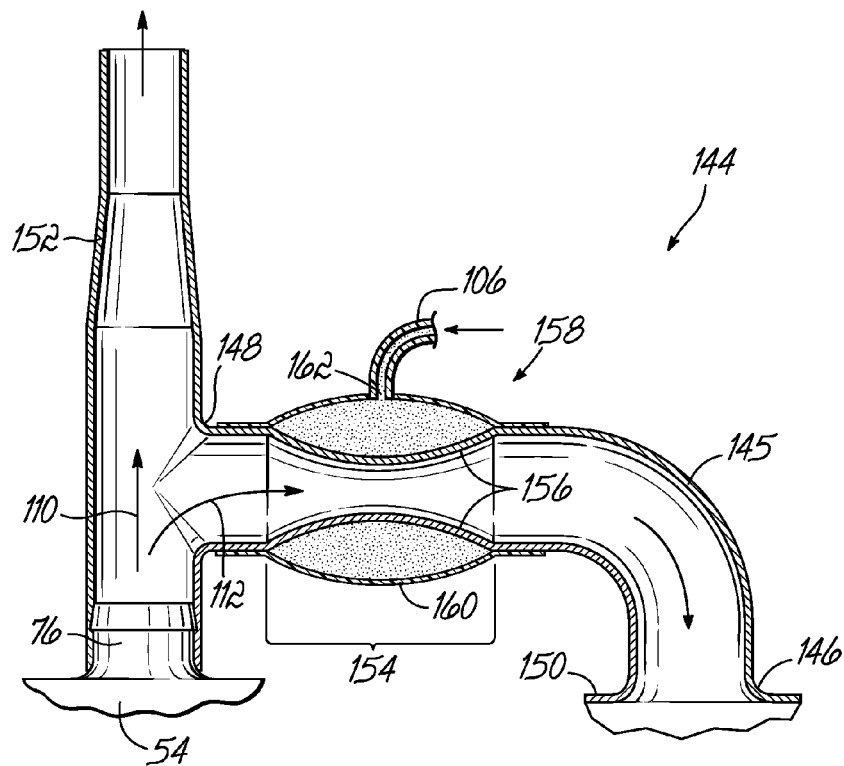
FIG. 5 is a cross-sectional view of a circulatory assist device including a by-pass shunt in accordance with yet another embodiment of the invention, showing the by-pass shunt configured to increase circulatory support.

FIG. 5 illustrates a by-pass shunt 144 in accordance with yet another embodiment of the invention. The by-pass shunt 144 includes a conduit 145 extending between first and second bifurcations 146, 148 that extending from the inflow and outflow conduits 150, 152, respectively. The conduit 145 includes a compliant portion 154 having at least one compressible wall 156. A by-pass flow restrictor 158, illustrated in FIG. 5 as an outer balloon 160, surrounds the compliant portion 154. For instance, the expandable material of the outer balloon 160 may be welded, or otherwise affixed, to lateral sides of the outer surface of the compliant portion 154 and such that the outer balloon 160 extends circumferentially around the compliant portion 154. A fluid port 162 fluidically connects the refill line 106 (FIG. 1) with volume that is between the outer balloon 160 and the outer surface of the compliant portion 154.

In use, injection of inflation fluid into the outer balloon 160 increases the fluidic pressure within the volume which inwardly compresses the compressible walls 156 of the compliant portion 154, decreases the diameter of the lumen of the compliant portion 154, and decreases the second portion of blood (arrow 112).

Figure 6:
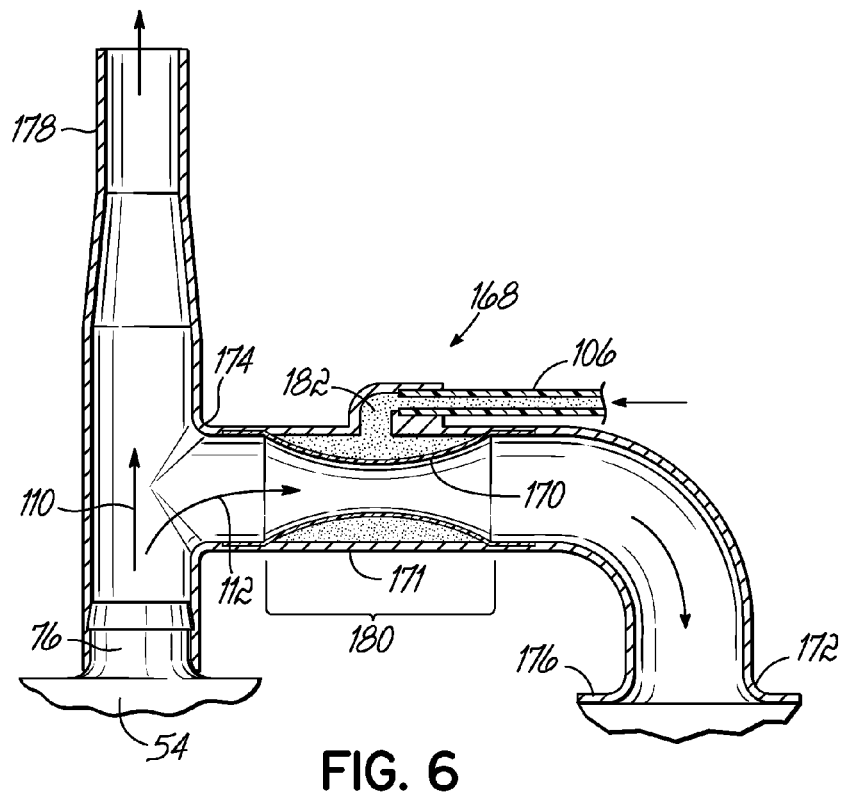
FIG. 6 is a cross-sectional view of a circulatory assist device including a by-pass shunt in accordance with another embodiment of the invention, showing the by-pass shunt configured to increase circulatory support.

FIG. 6 illustrates still another embodiment of a by-pass shunt 168 that is similar to the by-pass shunt 144 of FIG. 5; however, in FIG. 6, an inner balloon 170 is formed by welding or otherwise affixing the expandable material comprising the balloon 170 to the lateral sides of the inner surface of a conduit 171 that extends between the first and second bifurcations 172, 174 of the inflow and outflow conduits 176, 178, respectively. Accordingly, the walls comprising the by-pass shunt 168, including the conduit 171, may be fully reinforced. A compliant portion 180 is thus formed by the material comprising the inner balloon 170. The inner balloon 170 is inflatable through a fluid port 182 that is coupled to the refill line 106.

In use, injection of inflation fluid into the refill line 106 increases the fluidic pressure between the inner balloon 170 and the conduit 171. The resultant inflation of the inner balloon 170 decreases the diameter of the lumen of the compliant portion 180 and decreases the second portion of blood (arrow 112).

Figure 7:
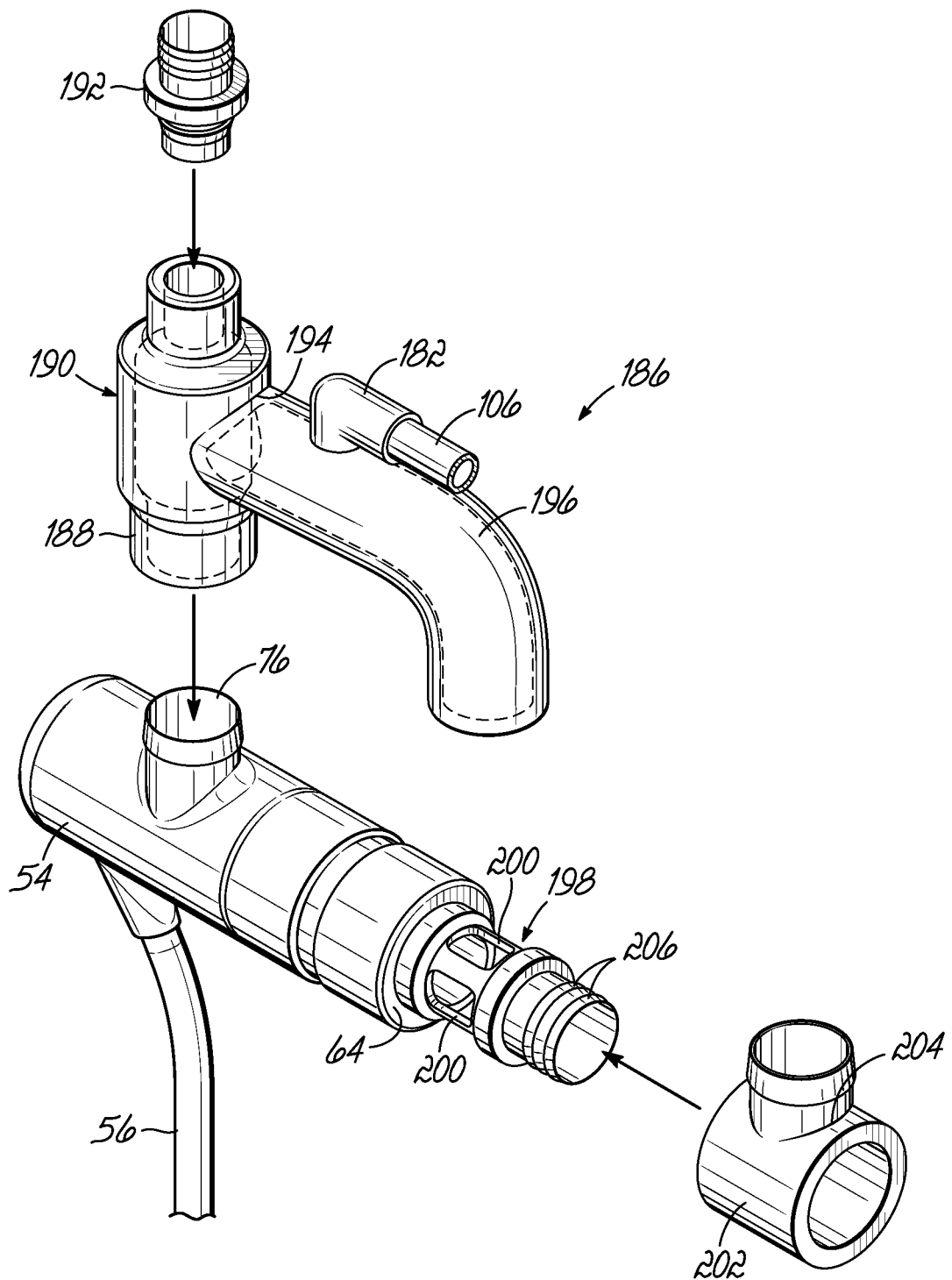
FIG. 7 is a perspective view of a circulatory assist device including an inline mixing chamber and an inflow distributor element according to one embodiment of the invention.
Figure 8:
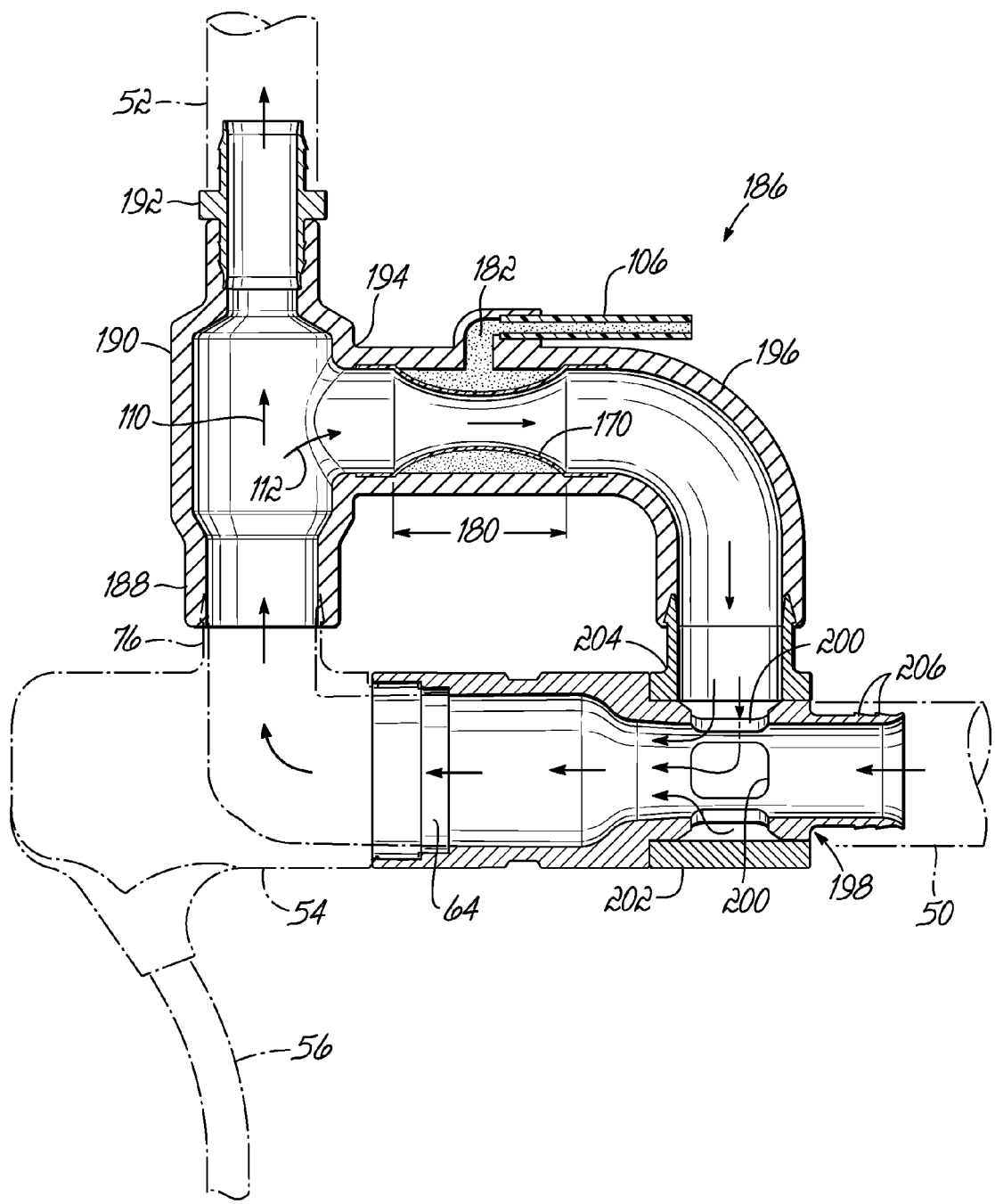
FIG. 8 is a cross-sectional view of the circulatory assist device of FIG. 7 with the second flow restricted to provide more circulatory support.
Figure 9:
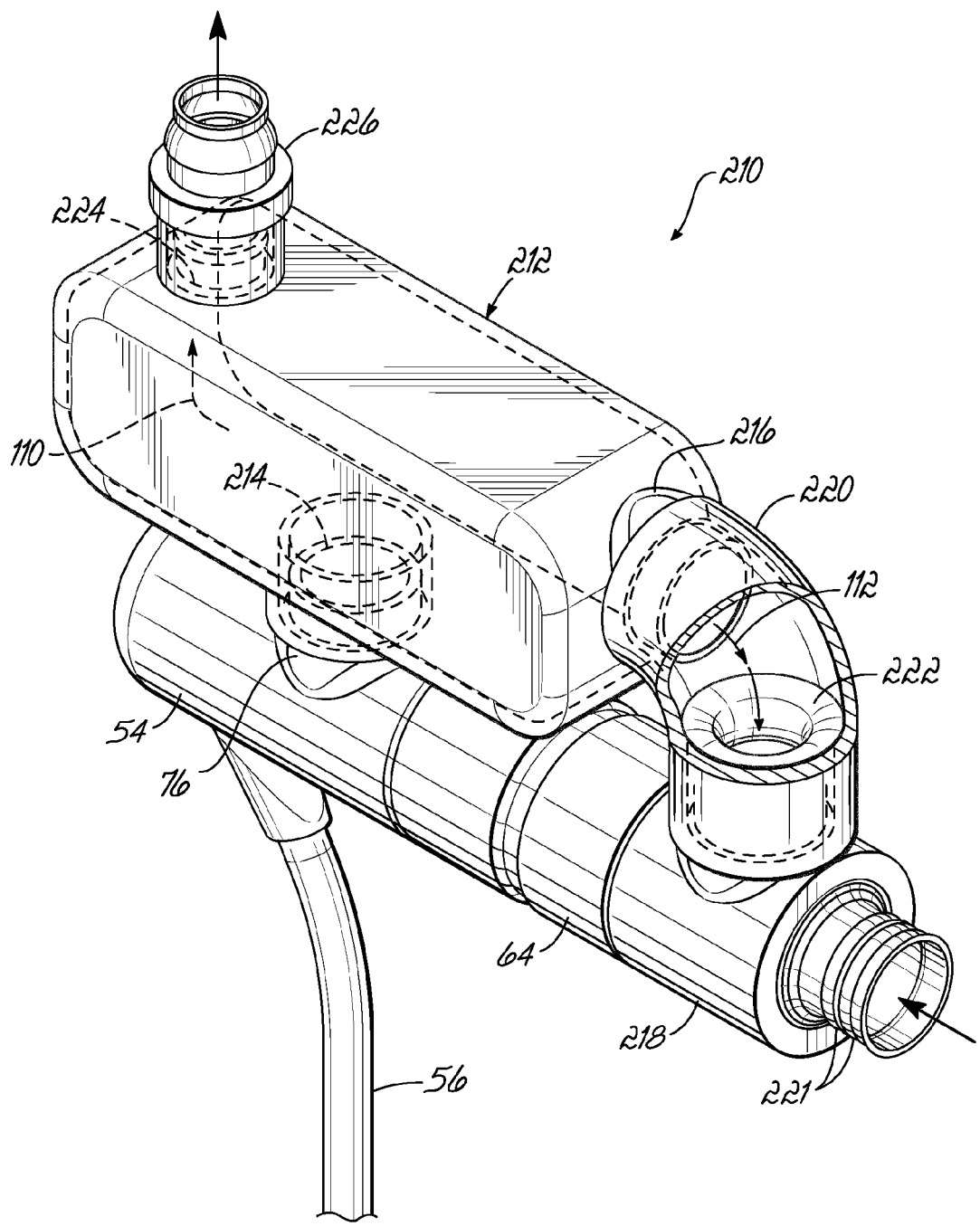
FIG. 9 is a perspective view of a circulatory assist device having an offset mixing chamber in accordance with one embodiment of the invention.

Turning now to FIGS. 7-9, various additional embodiments of by-pass shunts are illustrated and further includes a mechanism for mixing the blood flow moving through the by-pass shunt with blood entering the pump and the by-pass shunt from the a first vascular structure, for example, a chamber of the heart 12, the aorta 38, or a vena cava 32, 34 to a second vascular structure, such as the right subclavian artery 46 or other peripheral vessel. Mixing of the blood reduces the likelihood of blood stagnating within the by-pass shunt that would otherwise create a prothrombotic environment.

A first embodiment, illustrated in FIG. 7, includes a by-pass shunt 186 having an outflow conduit 188 with an inline mixing chamber 190 and, if necessary, an outflow cannula coupler 192 for coupling the by-pass shunt 186 to the outflow cannula 52 (FIGS. 1 and 8). The mixing chamber 190 may be constructed as an enlarged diameter portion of the outflow conduit 188 that is configured to hold a larger volume of blood than the outflow conduit 188 alone. A bifurcation 194 is formed at the mixing chamber 190 such that a portion of the larger volume of blood contained within the mixing chamber 190 may be diverted back to the inflow port 64 of the pump 54 through a bifurcated conduit 196 as described below.

The bifurcated conduit 196 may include a by-pass flow restrictor, which is specifically illustrated in FIG. 8 as the inner balloon 170 of FIG. 6; however any embodiment in accordance with the invention may be used.

The inflow port 64 of the pump 54 includes an inflow distributor element 198 that further contributes to the mixing of blood. The inflow distributor element 198 may be shaped as an annular fluid coupling that includes at least one aperture 200 so as to mix the second portion of blood (arrow 112) entering the inflow port 64 from the bifurcated conduit 196 with blood coming from the inflow cannula 50 (FIG. 1). An inflow adaptor 202 slides around the inflow distributor element 198 and provides a bifurcation connection 204 for coupling the distributor element 198 to the inflow cannula 50 (FIG. 1) and the bifurcated conduit 196. The proximal end of the distributor element 198 may include one or more barbs 206 for retaining the inflow cannula 50.

The by-pass shunt 186 of FIGS. 7 and 8 is particularly useful in adjusting the first and second portions of blood flow (arrows 110, 112) to accommodate the changing needs of the pediatric patient 14 (FIG. 1) while increasing the mixing capacity of incoming blood and reducing the risk of a prothrombotic event.

FIG. 9 illustrates a by-pass shunt 210 in accordance with yet another embodiment of the invention and having an off-set mixing chamber 212 that is coupled to the outflow port 76 of the pump 54. The off-set mixing chamber 212 includes a larger volume capacity for blood mixing than the inline mixing chamber 190 of FIG. 7. An inlet 214 of the off-set mixing chamber 212 is coupled to the outflow port 76 of the pump 54 such that the chamber 212 may reside above and have a substantially similar footprint as the mechanical pump 54. A first outlet 216 is directed toward, and coupled to, an adaptor 218 at the inflow port 64 of the pump 54 by an elbow joint 220. As shown, the adaptor 218 is further configured to receive the inflow cannula 50 (FIG. 1), such as including one or more barbs 221 for retaining the inflow cannula 50. The adaptor 218 may also include a by-pass restrictor 222, which is constructed in a manner similar to the inner balloon 170 (FIG. 6) for reducing the second flow of blood (arrow 112) as described previously. However, other embodiments of the flow construction may also be used. Furthermore, the placement of a restrictor for constricting the second flow of blood need not be limited to the particular illustrated position, but instead, may be positioned at the first outlet 216 of the off-set mixing chamber 212 or at a second outlet 224 of the off-set mixing chamber 212. The second outlet 224 may receive an adaptor 226 that is configured to receive the outflow cannula 52 (FIG. 1).

The by-pass shunt 210 of FIG. 9, like the embodiment of FIGS. 7 and 8, reduces the likelihood of stagnant blood flow that would lead to a prothrombotic environment while providing the adjustable blood flow to the arterial access site 78 (FIG. 1) as necessary for a growing pediatric patient 114 (FIG. 1).

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

What is claimed is:

1. A method of assisting cardiac output using a blood pumping system including an implantable mechanical pump having an inflow port and an outflow port and an implantable by-pass shunt having an inflow conduit coupled to the inflow port of the pump, an outflow conduit coupled to the outflow port of the pump, an intermediate conduit coupled to the inflow and outflow conduits, and a flow restrictor, the method comprising:
   coupling an inflow cannula to a first vascular structure of a patient;
   coupling an outflow cannula to a second vascular structure of the patient;
   coupling the inflow cannula to the inflow conduit of the shunt;
   coupling the outflow cannula to the outflow conduit of the shunt;
   implanting the pump and the shunt in the patient;
   operating the mechanical pump to direct blood flow from the first vascular structure toward the inflow conduit such that a first portion of the blood flow is directed from the outflow conduit to the second vascular structure and a second portion of the blood flow is directed from the outflow port into the intermediate conduit of the shunt and reenters the inflow port of the mechanical pump; and
   adjusting the flow rate of the first portion of the blood flow by adjusting a flow rate of the second portion of the blood flow; wherein adjusting the second portion of the blood flow includes adjusting the flow restrictor of the shunt while the pump is in use.

2. The method of claim 1 further comprising:
   decreasing the first portion of the blood flow by increasing the second portion of the blood flow.

3. The method of claim 1 further comprising:
   increasing the first portion of the blood flow by decreasing the second portion of the blood flow.

4. The method of claim 1, wherein the shunt includes a compliant portion having a first diameter state and a second diameter state that is smaller than the first diameter state, and restricting the second portion of the blood flow includes deforming the complaint portion of the shunt from the first diameter state to the second diameter state.

* * * * *